US011944600B2

(12) United States Patent
Whalley et al.

(10) Patent No.: US 11,944,600 B2
(45) Date of Patent: Apr. 2, 2024

(54) USE OF CANNABINOIDS IN THE TREATMENT OF A NEURODEGENERATIVE DISEASE OR DISORDER

(71) Applicant: GW Research Limited, Histon (GB)

(72) Inventors: Benjamin Whalley, Histon (GB); William Hind, Histon (GB); Royston Gray, Histon (GB); Javier Fernandez-Ruiz, Histon (GB); Eva De Lago, Madrid (ES); Carmen Rodriguez-Cueto, Madrid (ES); Laura Garcia-Toscano, Madrid (ES); Irene Santos-Garcia, Madrid (ES)

(73) Assignee: GW Research Limited, Histon (GB)

( * ) Notice: Subject to any disclaimer, the term of this patent is extended or adjusted under 35 U.S.C. 154(b) by 549 days.

(21) Appl. No.: 16/629,722

(22) PCT Filed: Jul. 10, 2018

(86) PCT No.: PCT/GB2018/051954
§ 371 (c)(1),
(2) Date: Jan. 9, 2020

(87) PCT Pub. No.: WO2019/012267
PCT Pub. Date: Jan. 17, 2019

(65) Prior Publication Data
US 2021/0077455 A1  Mar. 18, 2021

(30) Foreign Application Priority Data
Jul. 12, 2017  (GB) .................................. 1711190

(51) Int. Cl.
| A61K 31/353 | (2006.01) |
| A61K 31/00 | (2006.01) |
| A61K 31/05 | (2006.01) |
| A61K 31/192 | (2006.01) |
| A61K 31/575 | (2006.01) |
| A61K 36/185 | (2006.01) |
| A61P 25/28 | (2006.01) |

(52) U.S. Cl.
CPC .......... *A61K 31/658* (2023.05); *A61K 31/192* (2013.01); *A61K 31/353* (2013.01); *A61K 31/575* (2013.01); *A61K 36/185* (2013.01); *A61P 25/28* (2018.01)

(58) Field of Classification Search
CPC .... A61K 31/353; A61K 31/05; A61K 31/192; A61K 31/575; A61K 36/185; A61P 25/28
See application file for complete search history.

(56) References Cited

U.S. PATENT DOCUMENTS

| 5,804,592 | A | 9/1998 | Volicer |
| 2008/0181942 | A1 | 7/2008 | Zajicek |
| 2010/0239693 | A1* | 9/2010 | Guy ........................ A61P 25/28 |
| | | | 514/456 |
| 2010/0267733 | A1 | 10/2010 | Shytle et al. |

FOREIGN PATENT DOCUMENTS

| GB | 2434312 A | 7/2007 |
| GB | 2492487 A | 1/2013 |
| WO | WO 2007/083098 A1 | 7/2007 |
| WO | WO 2009/059277 A1 | 5/2009 |
| WO | WO 2013/005017 A1 | 1/2013 |

OTHER PUBLICATIONS

Lee Martin et al., Olesoxime, a cholesterol-like neuroprotectant for the potential treatment of amyotrophic lateral sclerosis, 13(8) IDrugs. 568-580 (2010) (Year: 2010).*
Giacoppo & Mazzon, 11(12) Neural Regen. Res. 1896-1899 (2016) (Year: 2016).*
Bordet et al., 3 Pharmaceuticals 345-368 (2010) (Year: 2010).*
Cao et al., The potential therapeutic effects of THC on Alzheimer's disease. J Alzheimers Dis. 2014;42(3):973-84. doi: 10.3233/JAD-140093.
Carroll et al., $\Delta^9$-tetrahydrocannabinol ($\Delta^9$-THC) exerts a direct neuroprotective effect in a human cell culture model of Parkinson's disease. Neuropathol Appl Neurobiol. Oct. 2012;38(6):535-47. doi: 10.1111/j.1365-2990.2011.01248.x.
Joerger et al., Single-dose pharmacokinetics and tolerability of oral delta-9-tetrahydrocannabinol in patients with amyotrophic lateral sclerosis. Drug Metab Lett. Jun. 1, 2012;6(2):102-8.
Lu et al., Current therapy of drugs in amyotrophic lateral sclerosis. Curr Neuropharmacol. 2016;14(4):314-21.
Nguyen et al., THC (Δ9-Tetrahydrocannabinol) exerts neuroprotective effect in glutamate-affected murine primary mesencephalic cultures through restoring mitochondrial membrane potential and anti-apoptosis involving CB1 receptor-dependent mechanism. Phytother. Res. Dec. 2016;30(12):2044-52. Epub Sep. 22, 2016. https://doi.org/10.1002/ptr.5712.
Raman et al., Amyotrophic lateral sclerosis: delayed disease progression in mice by treatment with a cannabinoid. Amyotroph Lateral Scler Other Motor Neuron Disord. Mar. 2004;5(1):33-9.

(Continued)

*Primary Examiner* — Timothy R Rozof
(74) *Attorney, Agent, or Firm* — Wolf, Greenfield & Sacks, P.C.

(57) ABSTRACT

The present invention relates to the use of cannabinoids in the treatment of a neurodegenerative disease or disorder. In particular the cannabinoids cannabidiolic acid (CBDA) and cannabidivarin (CBDV) were able to produce neuroprotective effects in a mouse model of neurodegenerative disease. In particular these effects were associated with the symptoms associated with amyotrophic lateral sclerosis (ALS). Furthermore, the combination of the cannabinoid tetrahydrocannabinol (THC) with the drug olexisome provided a synergistic disease modifying effect in a mouse model of neurodegenerative disease. In particular these effects were associated with the symptoms associated with ALS.

5 Claims, 9 Drawing Sheets

(56) References Cited

OTHER PUBLICATIONS

Weber et al., Tetrahydrocannabinol (THC) for cramps in amyotrophic lateral sclerosis: randomised, double-blind crossover trial. J Neurol Neurosurg Psychiatry. Oct. 2010;81(10):1135-40. doi: 10.1136/jnnp.2009.200642. Epub May 24, 2010.
PCT/GB2018/051954, Oct. 15, 2018, International Search Report and Written Opinion.
GB 1711190.7, Jul. 12, 2019, Combined Search and Examination Report.
PCT/GB2018/051954, Jan. 23, 2020, International Preliminary Report on Patentability.

* cited by examiner

Neurological score in male SOD-1 transgenic mice treated with CBD, THC, olesoxime or a combination of THC and olesoxime

USE OF CANNABINOIDS IN THE TREATMENT OF A NEURODEGENERATIVE DISEASE OR DISORDER

RELATED APPLICATION

This application is a national stage filing under 35 U.S.C. 371 of International Patent Application Serial No. PCT/GB2018/051954, filed Jul. 10, 2018, the entire contents of which is incorporated by reference herein in its entirety.

The present invention relates to the use of cannabinoids in the treatment of a neurodegenerative disease or disorder. In particular the cannabinoids cannabidiolic acid (CBDA) and cannabidivarin (CBDV) were able to produce neuroprotective effects in a mouse model of neurodegenerative disease. In particular these effects were associated with the symptoms associated with amyotrophic lateral sclerosis (ALS). Furthermore the combination of the cannabinoid tetrahydrocannabinol (THC) with the drug olesoxime provided a synergistic disease modifying effect in a mouse model of neurodegenerative disease. In particular these effects were associated with the symptoms associated with ALS.

BACKGROUND TO THE INVENTION

Neurodegenerative diseases or disorders include Alzheimer's disease; amyotrophic lateral sclerosis (ALS); Friedreich's ataxia; Huntington's disease; lewy body disease; motor neurone diseases (MND); Parkinson's disease and spinal muscular atrophy.

Degenerative nerve diseases can be serious or life-threatening, depending on the type. Most of these diseases have no cure and treatments are provided in an attempt to improve symptoms, relieve pain, and increase mobility.

Neurons are the building blocks of the nervous system which includes the brain and spinal cord. Neurons normally don't reproduce or replace themselves, so when they become damaged or die they cannot be replaced by the body.

Amyotrophic lateral sclerosis (ALS) is a rare group of neurological diseases that mainly involve the nerve cells (neurons) responsible for controlling voluntary muscle movement. Voluntary muscles produce movements like chewing, walking, breathing and talking. The disease is progressive and currently, there is no cure for ALS and no effective treatment to halt, or reverse, the progression of the disease.

ALS belongs to a wider group of disorders known as motor neuron diseases, which are caused by gradual deterioration (degeneration) and death of motor neurons. Motor neurons are nerve cells that extend from the brain to the spinal cord and to muscles throughout the body. These motor neurons initiate and provide vital communication links between the brain and the voluntary muscles.

Messages from motor neurons in the brain (called upper motor neurons) are transmitted to motor neurons in the spinal cord and to motor nuclei of brain (called lower motor neurons) and from the spinal cord and motor nuclei of brain to a particular muscle or muscles.

In ALS, both the upper motor neurons and the lower motor neurons degenerate or die, and stop sending messages to the muscles. Unable to function, the muscles gradually weaken, start to twitch and waste away. Eventually, the brain loses its ability to initiate and control voluntary movements.

Early symptoms of ALS usually include muscle weakness or stiffness. Gradually all muscles under voluntary control are affected, and individuals lose their strength and the ability to speak, eat, move, and breathe.

Most people with ALS die from respiratory failure, usually within 3 to 5 years from when the symptoms first appear. Only 10 percent of people with ALS survive for 10 or more years.

There is currently only one drug that has been approved by the FDA for the treatment of ALS. This medication, riluzole, delays the onset of ventilator-dependence or tracheostomy in some patients and may increase survival by approximately two to three months.

Other medications that are already approved for other indications such as: edaravone, olesoxime, talampanel, or ceftriaxone have been indicated in pre-clinical studies to be of potential benefit to treat symptoms of ALS.

Different cannabinoid compounds: Delta-9-tetrahydrocannabinol (D9-THC); cannabinol (CBN); selective CB2 receptor agonists; and fatty acid amide hydrolase (FAAH) inhibitors have been shown to be neuroprotective in an experimental model of ALS.

The patent application WO 2007/083098 describes the use of CBD and THC botanical drug substance (BDS) on hippocampal neurones. Such cell binding studies suggested that these BDS may have a neuroprotective effect.

A small trial of 27 patients with ALS was conducted with a synthetic THC dronabinol. Results indicated that 5 mg of THC twice daily failed to have a significant effect on the cramps associated with ALS.

The present invention provides data to demonstrate the effect of novel cannabinoids in animal models of ALS. It further demonstrates the effectiveness of a combination of cannabinoids and medications commonly used in the treatment of ALS.

BRIEF SUMMARY OF THE DISCLOSURE

In accordance with a first aspect of the present invention there is provided one or a combination of the phytocannabinoids cannabidiolic acid (CBDA); cannabidivarin (CBDV); and tetrahydrocannabinol (THC) for use in the treatment of a neurodegenerative disease or disorder.

Neurodegenerative diseases or disorders include Alzheimer's disease; amyotrophic lateral sclerosis (ALS); Friedreich's ataxia; Huntington's disease; lewy body disease; motor neurone diseases (MND); Parkinson's disease and spinal muscular atrophy.

Preferably the neurodegenerative disease or disorder is amyotrophic lateral sclerosis (ALS).

Preferably the phytocannabinoids are for use in combination with medications used or tested in the treatment of ALS. Such medications include one or more of riluzole, edaravone, olesoxime, talampanel, or ceftriaxone.

In a further embodiment the specific combination of the phytocannabinoid THC is used with olesoxime.

Preferably the phytocannabinoid is present as an extract of the cannabis plant. More preferably the extract of the cannabis plant is a botanical drug substance (BDS).

Alternatively the phytocannabinoid is present as a highly purified, isolated or synthetic cannabinoid.

In accordance with a second aspect of the present invention there is provided a method of treating a patient with a neurodegenerative disease or disorder comprising administering one or a combination of the phytocannabinoids cannabidiolic acid (CBDA); cannabidivarin (CBDV); and tetrahydrocannabinol (THC) to the patient in need thereof.

Preferably the neurodegenerative disease or disorder is amyotrophic lateral sclerosis (ALS). More preferably the patient is a human.

BRIEF DESCRIPTION OF THE DRAWINGS

Embodiments of the invention are further described hereinafter with reference to the accompanying drawings, in which.

DEFINITIONS

Figure 1:
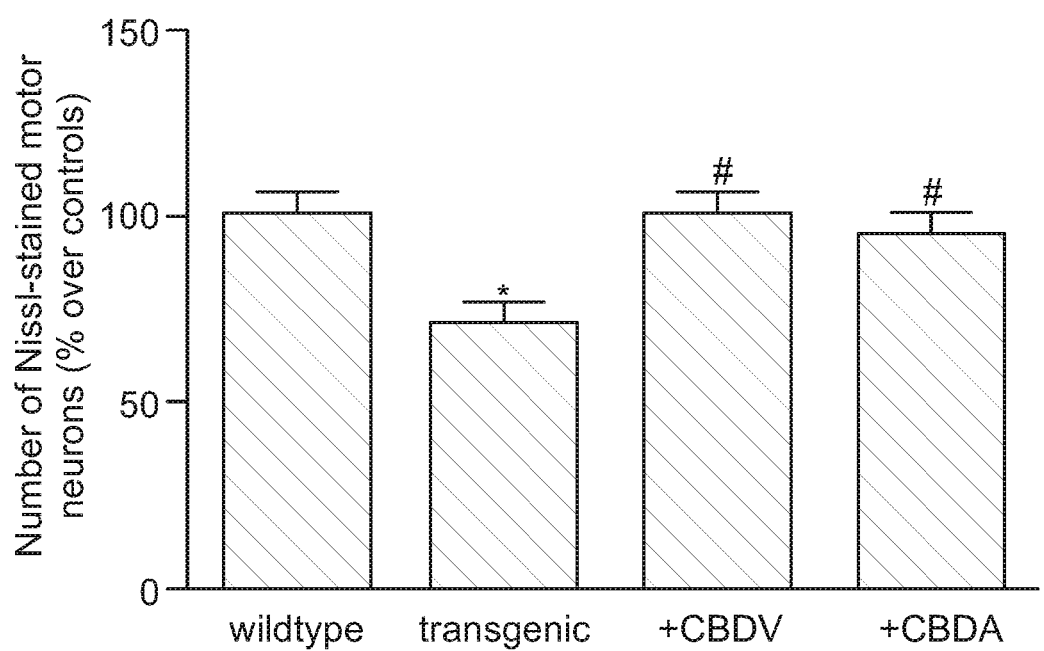
FIG. 1 shows the number of spinal motor neurons in wildtype, transgenic and transgenic mice treated with CBDV or CBDA.

Definitions of some of the terms used to describe the invention are detailed in Table 1 below:

The cannabinoids described in the present application are listed below along with their standard abbreviations.

TABLE 1

| Cannabinoids and their abbreviations | | |
|---|---|---|
| CBD | Cannabidiol | 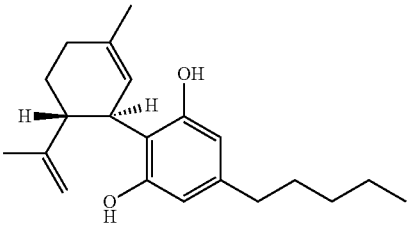 [SMILES: C=C(C)[C@@H]1CCC(C)=C[C@H]1c1c(O)cc(CCCCC)cc1O] |
| CBDA | Cannabidiolic acid | 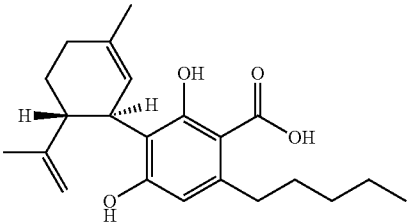 [SMILES: C=C(C)[C@@H]1CCC(C)=C[C@H]1c1c(O)cc(CCCCC)c(C(=O)O)c1O] |
| CBDV | Cannabidivarin | 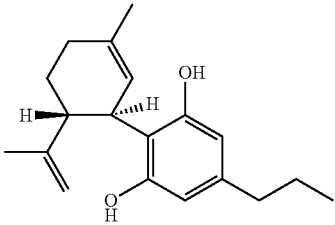 [SMILES: C=C(C)[C@@H]1CCC(C)=C[C@H]1c1c(O)cc(CCC)cc1O] |
| THC | Tetrahydrocannabinol | 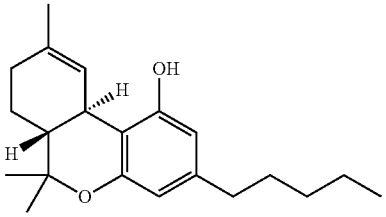 [SMILES: CCCCCc1cc(O)c2c(c1)OC(C)(C)[C@@H]1CCC(C)=C[C@@H]21] |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the cannabis plant. The phytocannabinoids can be isolated from plants to produce a highly purified extract or can be reproduced synthetically.

"Botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug substance derived from one or more plants, algae, or macroscopic fungi. It is prepared from botanical raw materials by one or more of the following processes: pulverisation, decoction, expression, aqueous extraction, ethanolic extraction, or other similar processes. A botanical drug substance does not include a highly purified or chemically modified substance derived from natural sources. Thus, in the case of cannabis, "botanical drug substances" derived from cannabis plants do not include highly purified, Pharmacopoeial grade cannabinoids.

"Highly purified cannabinoids" are defined as cannabinoids that have been extracted from the cannabis plant and purified to the extent that other cannabinoids and non-cannabinoid components that are co-extracted with the cannabinoids have been removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

DETAILED DESCRIPTION

The following examples provide evidence for the efficacy of certain phytocannabinoids in the treatment of neurodegenerative diseases or disorders. Two different mouse models of amyotrophic lateral sclerosis (ALS) have been used to demonstrate the effectiveness of the cannabinoids as neuroprotectants. Furthermore there is evidence presented to demonstrate that a combination of a phytocannabinoid with a compound used in the treatment of ALS is able to modify the neurodegenerative disease.

Example 1: Efficacy of Cannabinoids in Recovery of Symptoms in a Transgenic Mouse Model of Amyotrophic Lateral SCLEROSIS (ALS)

Materials and Methods
Mouse Model

A transgenic mouse model of ALS, TDP-43, was used to determine the effects of the cannabinoids in treatment of symptoms of ALS.

The TDP-43 transgenic and wild-type mice were subjected to genotyping to identify the presence of mutant TDP-43 gene. These mice were used for a chronic i.p. treatment (from 60 days of age up to the age of 90 days) with cannabinoid or vehicle.

All studies were conducted in male mice (n=6-8 subjects in each experimental group).

Drug Treatments

The neuroprotective effects of 2 different phytocannabinoids (CBDV and CBDA) were investigated. The cannabinoids were administered at a dose of 10 mg/kg/day.
Symptom Recording and Analyses Animals were recorded for neurological decline by testing rotarod performance and observing limb clasping during the whole treatment period. The weight of the animals was also recorded during the treatment period.

Animals were euthanized at the end of the treatment period and their spinal cords collected for biochemical and histopathological analyses.
Statistics Data were assessed using one-way (immunostaining data) or two-way (rotarod data) ANOVA followed by an appropriate post-hoc test (Student Newman-Keuls for immunostaining data, and Bonferroni for behavioural data) significance was reported at $p \leq 0.05$. Data shown in the figures represent "$p<0.01$, ***$p<0.001$.
Results TDP-43 transgenic mice experience a loss of Nissl-stained motor neurons in the spinal cord. This was almost completely recovered by treatment with CBDA and CBDV ($p<0.05$ between vehicle-treated and CBDA- or CBDV-treated transgenic mice) as shown in FIG. 1.

The reduction of spinal motor neurons in TDP-43 transgenic mice was associated with an elevation in the number of astrocytes labelled with Glial fibrillary acidic protein (GFAP) immunostaining, in particular activated astrocytes identified by analysis of their morphological characteristics (e.g. increased cell shape and size, reduction in the length of processes).

Figure 2:
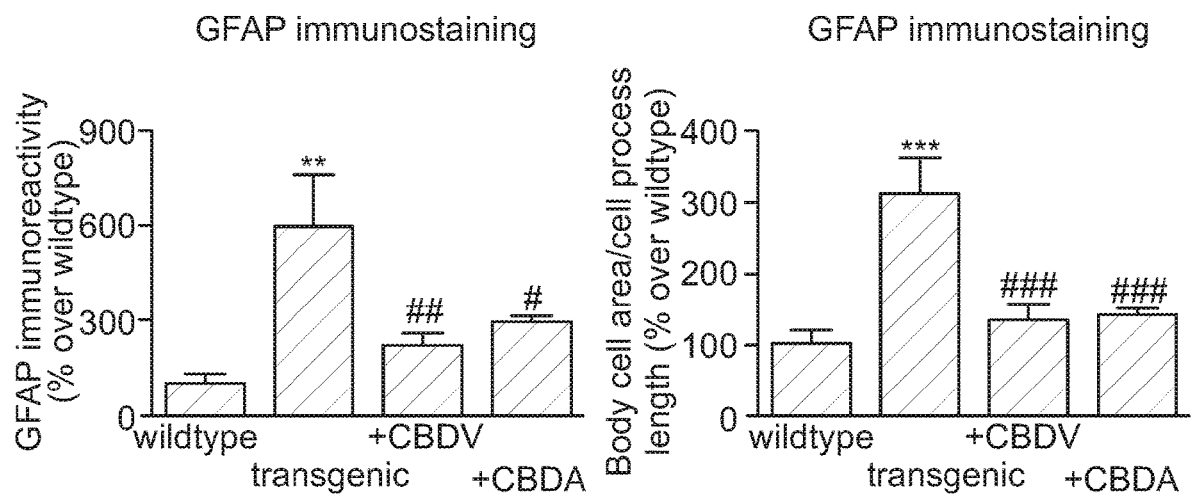
FIG. 2 shows GFAP immunostaining of spinal motor neurons in wildtype, transgenic and transgenic mice treated with CBDV or CBDA.

Treatment with either CBDA or CBDV reduced total immunoreactivity for GFAP and the ratio between cell body area and process length reflecting that these cannabinoids were able to facilitate the shift from the activated to the resting state in these cells as is shown in FIG. 2.

The number of microglial cells in the spinal cord was quantified using lba-1 immunostaining, and again differentiating resting and activated cells through the analysis of their morphological characteristics (e.g. cell shape and size, type of processes). There was a significant increase in lba-1 immunostaining in cell bodies, accompanied by a reduction in the cell processes, in TDP-43 transgenic mice versus wild-type animals, reflecting the activation of microglial cells. This was also seen when the ratio between cell body area and cell process length was calculated.

Figure 3:
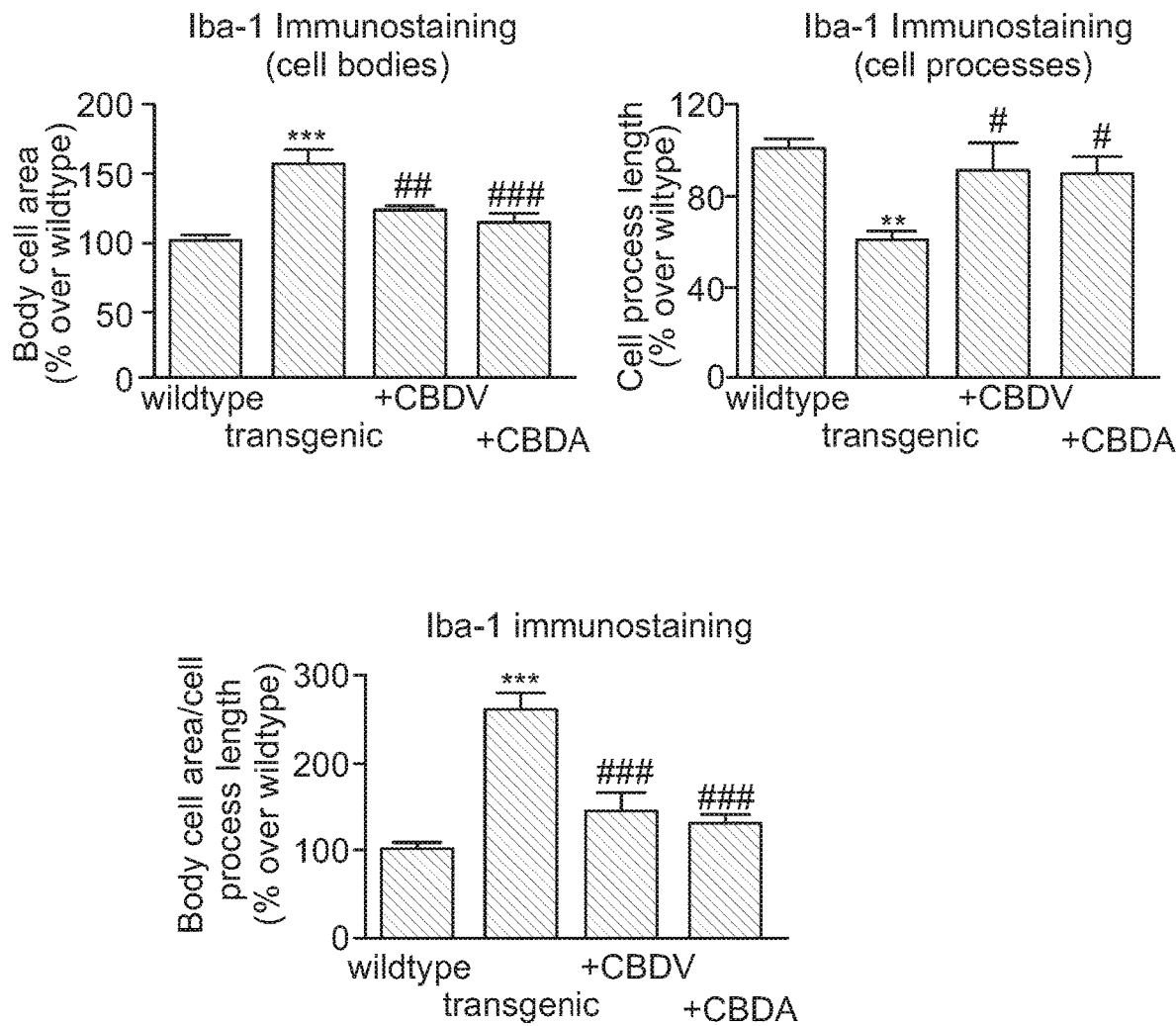
FIG. 3 shows lba-1 immunostaining of spinal motor neurons in wildtype, transgenic and transgenic mice treated with CBDV or CBDA.

FIG. 3 demonstrates that treatment with CBDA or CBDV reversed the changes found in TDP-43 transgenic mice in all parameters determined.

The rotarod test was utilised to quantify the muscle weakness characteristic of TDP-43 transgenic mice. A reduction in the rotarod performance (reduced latency to fall from the rod) was seen in vehicle-treated TDP-43 transgenic mice as soon as the disease progressed.

Figure 4:
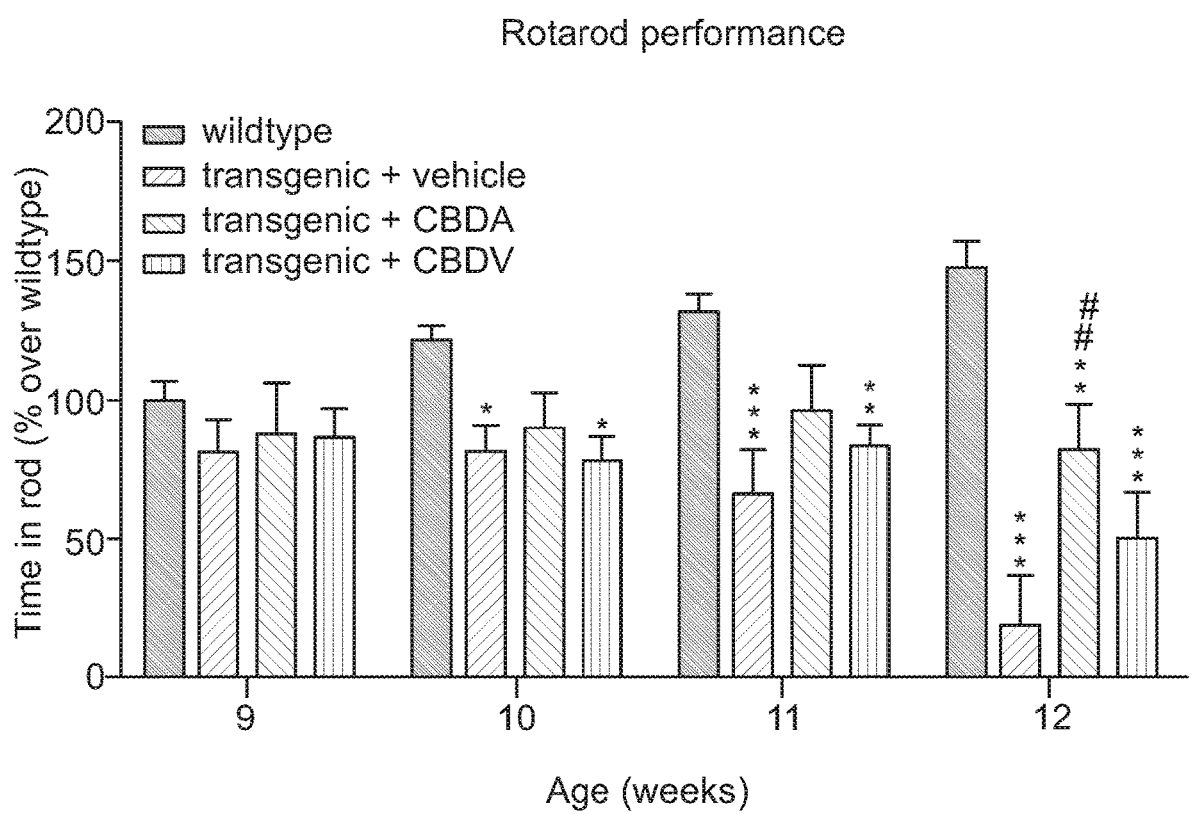
FIG. 4 shows the latency to fall measured in the rotarod test in adult male wildtype and transgenic mice and transgenic mice treated with CBDV or CBDA.

Treatment with CBDA attenuated the rotarod worsening even at the advanced stages of the disease as is demonstrated in FIG. 4.

At 12 weeks of age, motor performance in vehicle, CBDA and CBDV treated TDP-43 mice was significantly impaired compared to wild type, however CBDA treated TDP-43 mice displayed significantly superior performance on the rotarod compared to vehicle.

Figure 5:
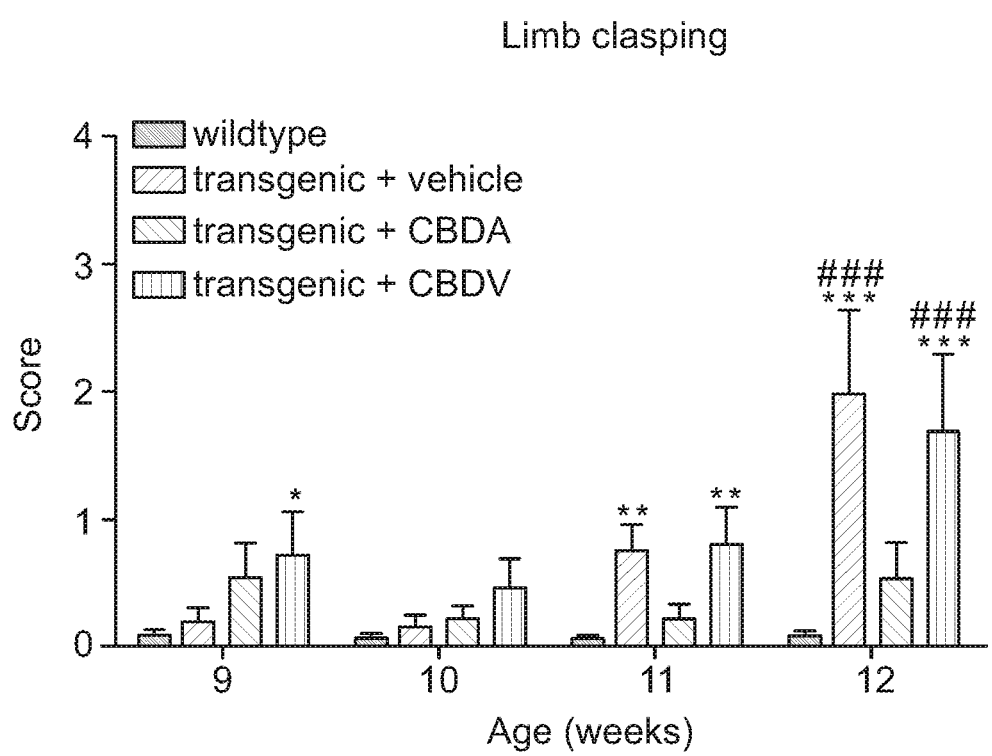
FIG. 5 shows the frequency of limb clasping measured in adult male wildtype and transgenic mice and transgenic mice treated with CBDV or CBDA.

Similar positive effects with CBDA were found in the analysis of limb clasping, which increased significantly in TDP-43 transgenic mice once the disease progressed. This increase was strongly and significantly attenuated after CBDA treatment as is shown in FIG. 5.

Figure 6:
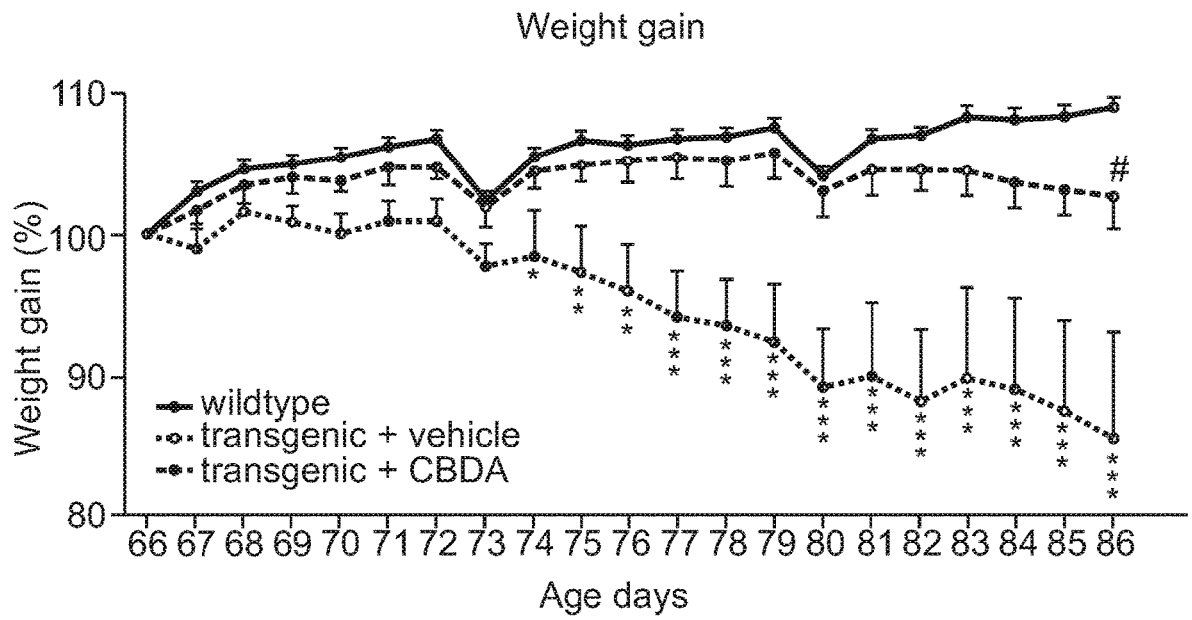
FIG. 6 shows the weight gain in adult male wildtype and transgenic mice and transgenic mice treated with CBDV or CBDA.
Figure 6:
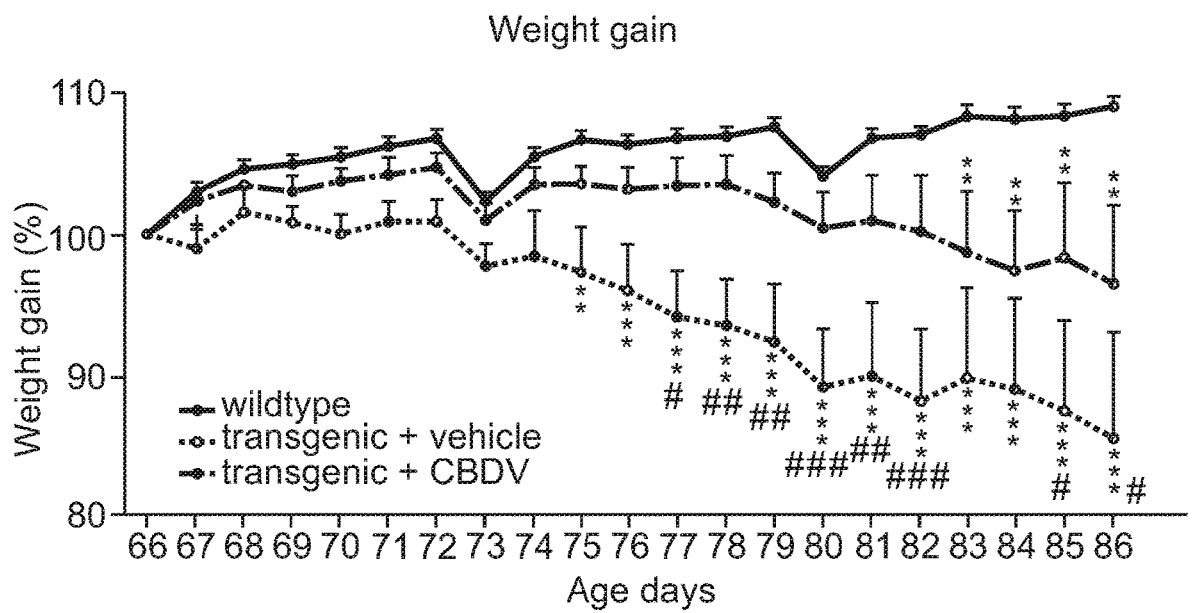

The weight gain of animals was also monitored, this is a variable which is frequently used to monitor disease progression in animal models of ALS. Both phytocannabinoids were able to prevent (CBDA) or reduce (CBDV) the marked weight loss exhibited by TDP-43 transgenic mice as shown in FIG. 6A (CBDA) and FIG. 6B (CBDV).

Conclusions

CBDA and CBDV were able to prevent deterioration of spinal motor neurons in TDP-43 transgenic mice.

A clear functional recovery at the neurological level (rotarod performance and limb clasping) was seen in addition to prevent or reduce the marked weight loss that occurs in the animals which are genetically bred to develop ALS symptoms.

Such data suggests that these cannabinoids provide a novel and effective treatment option for ALS.

Example 2: Efficacy of a Cannabinoid Extract in Combination with Olesoxime on Recovery of Symptoms in a Transgenic Mouse Model of Amyotrophic Lateral Sclerosis (ALS)

Materials and Methods

Mouse Model

A transgenic mouse model of ALS, SOD1, was used to determine the effects of the combined treatment of a drug used in the treatment of ALS, olesoxime, with THC.

mSOD1-transgenic (G93A) and wild-type mice were subjected to genotyping to identify the presence of mutant SOD-1. These mice were used for chronic treatment (from 10 weeks of age up to the age of 21 weeks) with test article or vehicle.

All studies were conducted in male mice (n=6-8 subjects in each experimental group).

Drug Treatments

The treatment groups were as follows: THC-BDS (10 mg/kg; i.p.); CBD-BDS (10 mg/kg; i.p); olesoxime (3 mg/kg; s.c.); a combination of THC-BDS and olesoxime; and vehicle. A group of wild-type animals were also treated with vehicle.

Symptom Recording and Analyses

Animals were recorded for neurological decline by testing rotarod performance during the whole treatment period. Animals were recorded for neurological decline (using a previously published ALS-related neurological scale; de Munck et al., 2013).

Animals were euthanized at the end of the treatment period and their spinal cords collected for biochemical and histopathological analyses.

Statistics

Data were assessed using one-way (immunostaining data) or two-way (rotarod data) ANOVA followed by an appropriate post-hoc test (Student Newman-Keuls for immunostaining data, and Bonferroni for behavioural data) significance was reported at $p \le 0.05$. Data shown in the figures represent "$p<0.01$, ***$p<0.001$ Results As expected, SOD-1 transgenic mice experienced a reduction in the rotarod performance, which was strongly marked towards the end of the treatment period.

Treatment with CBD-BDS was unable to increase the time spent by animals in the rod, suggesting a lack of effect on the symptoms of ALS.

Figure 7:
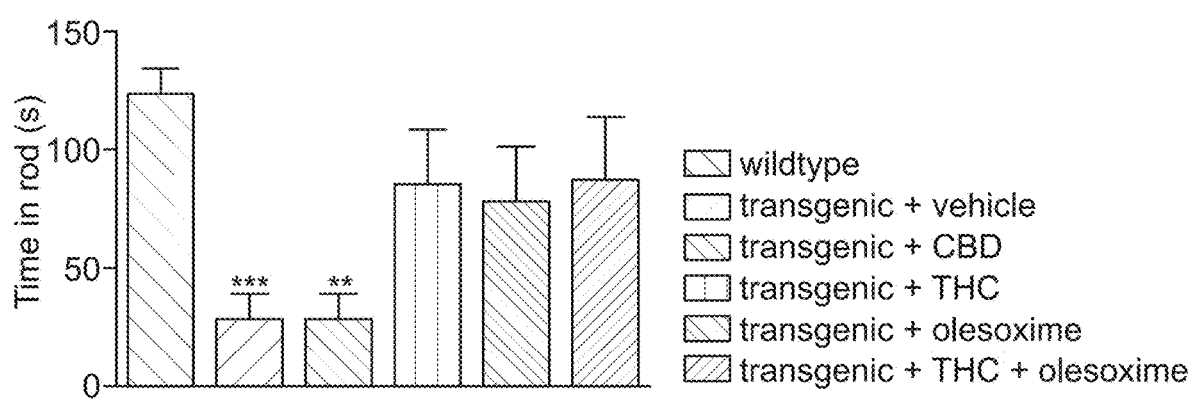
FIG. 7 shows rotarod performance in male SOD-1 transgenic mice treated with CBD, THC, olesoxime or a combination of THC and olesoxime.

Treatment with THC-BDS, olesoxime or the combination of the two were able to attenuate the effect, enabling the animals treated with these compounds wo spend greater time on the rotarod. A similar effect was seen in all three groups as is shown in FIG. 7.

Figure 8:
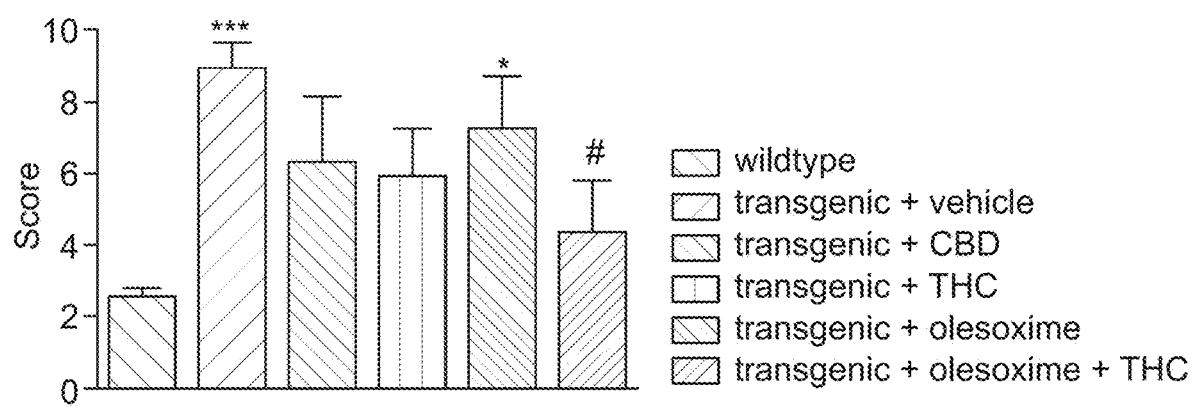
FIG. 8 shows Neurological score in male SOD-1 transgenic mice treated with CBD, THC, olesoxime or a combination of THC and olesoxime.

There was an elevated Neurological Score in SOD-1 mutant mice, which reflects neurological decline. This was not significantly improved by CBD-BDS. It was observed that THC-BDS and olesoxime given alone also displayed non-significant trends towards a reduced score, but their combination significantly reduced the elevated score recorded in SOD-1 mutant mice by 50%, indicating that this combination had synergistic effects (FIG. 8).

The number of motor neurons in the ventral horn of the spinal cord was quantified using Nissl staining. Mutant SOD-1 mice showed a significant reduction in the number of Nissl-stained motor neurons. The treatment of these mice with CBD-BDS showed a slight increase in neurons, whereas treatment with THC-BDS or olesoxime proved statistically significant compared to mutant SOD-1 mice treated with vehicle.

Figure 9:
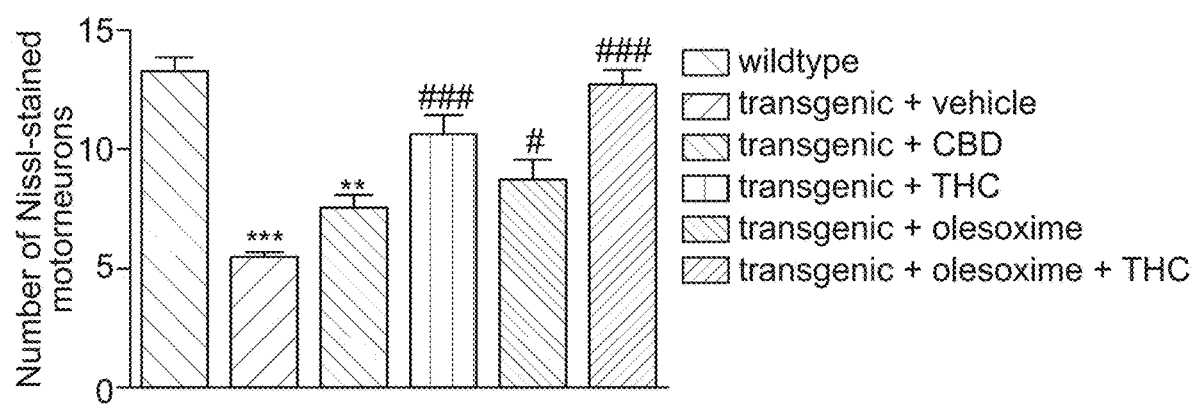
FIG. 9 shows Number of motor neurons stained with Nissl in the ventral horn of the spinal cord in male SOD-1 transgenic mice treated with CBD, THC, olesoxime or a combination of THC and olesoxime.

Surprisingly, mice treated with the combination of THC-BDS and olesoxime reached a complete recovery with a number of motor neurons to a number similar to the wild-type mice as demonstrated in FIG. 9.

CONCLUSIONS

These data suggest that THC-BDS is effective in improving the deteriorated rotarod performance shown by SOD-1 mutant mice, and, combined with olesoxime, it is also able to improve the neurological decline of these mutant mice.

The ability of the combination to provide a complete recovery in the number of motor neurons in the transgenic mice is suggestive of an unexpected disease modifying effect.

The invention claimed is:

1. A method of treating a patient with amyotrophic lateral sclerosis (ALS) comprising administering to the patient tetrahydrocannabinol (THC) in combination with olesoxime.

2. The method of claim 1, wherein the THC is present as an extract of a cannabis plant.

3. The method of claim 2, wherein the extract of the cannabis plant is a botanical drug substance (BDS).

4. The method of claim 1, wherein the THC is present as a highly purified, isolated or synthetic cannabinoid.

5. The method of claim 2, wherein the THC is present as a highly purified, isolated or synthetic cannabinoid.

* * * * *